United States Patent
Ide

(10) Patent No.: US 10,813,543 B2
(45) Date of Patent: Oct. 27, 2020

(54) INSERTION PORTION OF ENDOSCOPE

(71) Applicant: OLYMPUS CORPORATION, Tokyo (JP)

(72) Inventor: Yuka Ide, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/794,382

(22) Filed: Feb. 19, 2020

(65) Prior Publication Data

US 2020/0178778 A1    Jun. 11, 2020

Related U.S. Application Data

(63) Continuation of application No. PCT/JP2018/026077, filed on Jul. 10, 2018.

(30) Foreign Application Priority Data

Sep. 1, 2017   (JP) .................................. 2017-168392

(51) Int. Cl.
*A61B 1/05*     (2006.01)
*H04N 5/225*    (2006.01)

(52) U.S. Cl.
CPC ............ *A61B 1/05* (2013.01); *H04N 5/2251* (2013.01); *H04N 2005/2255* (2013.01)

(58) Field of Classification Search
CPC ...................................................... A61B 1/05
See application file for complete search history.

(56) References Cited

U.S. PATENT DOCUMENTS

| | | | | |
|---|---|---|---|---|
| 4,677,471 A | * | 6/1987 | Takamura | A61B 1/05 348/373 |
| 5,797,836 A | * | 8/1998 | Lucey | A61B 1/00179 600/109 |
| 8,668,637 B2 | * | 3/2014 | Tanahashi | A61B 1/00039 600/112 |
| 9,158,103 B2 | | 10/2015 | Kato | |
| 9,398,843 B2 | * | 7/2016 | Morimoto | A61B 1/00087 |
| 10,085,616 B2 | * | 10/2018 | Takemoto | A61B 1/00098 |

(Continued)

FOREIGN PATENT DOCUMENTS

| EP | 2614767 A1 | 7/2013 |
|---|---|---|
| EP | 2695567 A1 | 2/2014 |

(Continued)

OTHER PUBLICATIONS

NPL Google Search; 2020 (Year: 2020).*
International Search Report dated Oct. 2, 2018 issued in PCT/JP2018/026077.

*Primary Examiner* — Luis Perez-Fuentes
(74) *Attorney, Agent, or Firm* — Scully, Scott, Murphy & Presser, P.C.

(57) ABSTRACT

An insertion portion of an endoscope includes: an image pickup unit having an observation unit and an image pickup cable; and a distal end frame member having a first hole and a second hole and having a contact surface with which a proximal end portion is brought into contact when the image pickup cable is provided in the second hole. The second hole has a shape in which the image pickup cable is rotatable together with the observation unit in a state where the image pickup cable is provided in the second hole.

6 Claims, 5 Drawing Sheets

(56) References Cited

U.S. PATENT DOCUMENTS

| 2012/0323073 | A1* | 12/2012 | Azuma | A61B 1/05 |
| | | | | 600/110 |
| 2013/0172674 | A1 | 7/2013 | Kennedy, II et al. | |
| 2013/0184525 | A1 | 7/2013 | Kojima | |
| 2014/0362200 | A1* | 12/2014 | Kanamori | A61B 1/05 |
| | | | | 348/70 |
| 2020/0107708 | A1* | 4/2020 | Amano | A61B 1/05 |

FOREIGN PATENT DOCUMENTS

| JP | 2004-008638 A | 1/2004 |
| JP | 2007-289231 A | 11/2007 |
| JP | 2010-005269 A | 1/2010 |
| JP | 2012-055525 A | 3/2012 |
| JP | 2014-033730 A | 2/2014 |
| WO | WO 2012/032935 A1 | 3/2012 |
| WO | WO 2013/101901 A1 | 7/2013 |

\* cited by examiner

R3<R5

INSERTION PORTION OF ENDOSCOPE

CROSS REFERENCE TO RELATED APPLICATION

This application is a continuation application of PCT/JP2018/026077 filed on Jul. 10, 2018 and claims benefit of Japanese Application No. 2017-168392 filed in Japan on Sep. 1, 2017, the entire contents of which are incorporated herein by this reference.

BACKGROUND OF INVENTION

1. Field of the Invention

The present invention relates to an insertion portion of an endoscope including an image pickup unit and a distal end frame member in which the image pickup unit is provided.

2. Description of the Related Art

In recent years, endoscopes have been widely used in a medical field and an industrial field. By inserting an elongated insertion portion into a subject/object to be examined, the endoscope is able to perform observation, treatment, and the like of an object in the subject/object to be examined an image of which is picked up by an image pickup unit provided in the insertion portion.

The image pickup unit is well known to have an observation unit, which is a large outer size member having an optical system and an image pickup unit to pick up an image of an object in a subject/object to be examined formed on the optical system, and an image pickup cable which is a small outer size member extended from the observation unit.

The observation unit of the image pickup unit and the distal end side of the image pickup cable of the image pickup unit are well known to be provided in a distal end frame member provided at a distal end portion of an insertion portion, and are disclosed in, for example, Japanese Patent Laid-Open Publication No. 2007-289231.

SUMMARY OF THE INVENTION

An insertion portion of an endoscope according to an aspect of the present invention includes: an image pickup unit having a non-circular large outer size member having a first central axis and a first outer size, and a small outer size member having a second central axis offset from the first central axis, the small outer size member having a second outer size smaller than the first outer size and connected to a proximal end of the large outer size member; and a distal end frame member having a first hole in which the large outer size member is provided, and a second hole provided in a proximal end of the first hole and in which the small outer size member is provided. The second hole has a shape in which the small outer size member is rotatable together with the large outer size member in a state where the small outer size member is provided in the second hole.

DETAILED DESCRIPTION OF THE PREFERRED EMBODIMENT

Hereinafter, embodiments of the present invention will be described with reference to the accompanying drawings. Note that the drawings are schematic, and a relationship between a thickness and a width of each of sections, a proportion of respective thicknesses of the sections, and the like respectively differ from actual ones. Among the drawings, which differ in dimensional relationship and proportion, may be respectively included.

Figure 1:
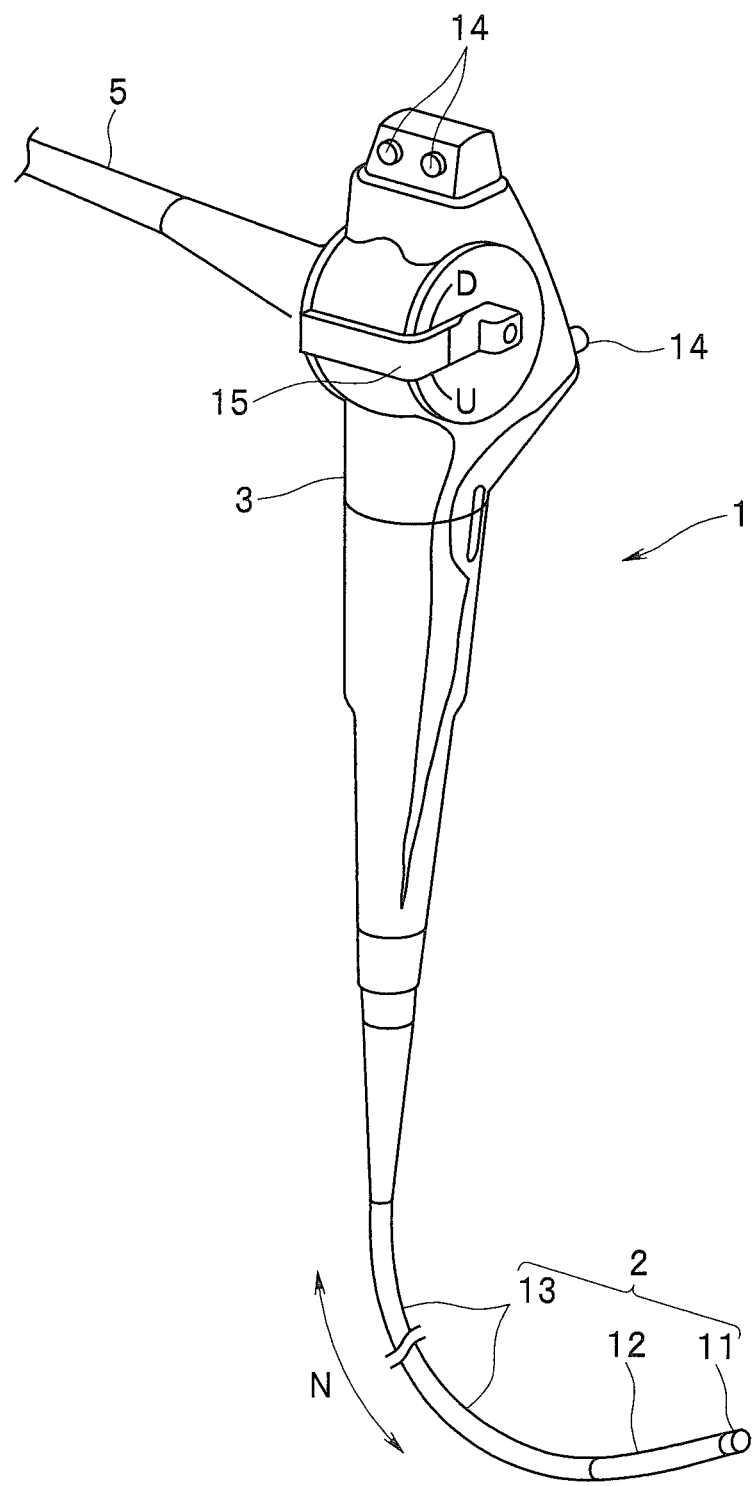
FIG. 1 is a partial perspective view of an endoscope having an insertion portion of an endoscope according to a present embodiment.

FIG. 1 is a partial perspective view of an endoscope including an insertion portion of an endoscope according to a present embodiment.

As illustrated in FIG. 1, an endoscope 1 includes, as main components, an insertion portion 2 which is elongated along a longitudinal axis direction N and which has flexibility, an operation portion 3 which is provided on a proximal end side of the insertion portion 2, a universal cord 5 which extends from the operation portion 3, and a connector (not illustrated) which is provided at an extended end of the universal cord and connected to an image processing apparatus, a light source device, and the like (all not illustrated).

The insertion portion 2 includes, as main components, in the order from a distal end side, a distal end portion 11 in which an observation unit 151 (see FIG. 3) described later is provided, a bending portion 12 which is provided on a proximal end side of the distal end portion 11 and bendable in a plurality of directions, for example, two directions, and a flexible tube portion 13 which is provided on a proximal end side of the bending portion 12. The bending portion may be configured to be bendable in four directions.

The operation portion 3 is provided with a remote switch 14 for instructing image control such as freezing and releasing, a bending operation lever 15 for bending the bending portion 12, and the like.

Figure 2:
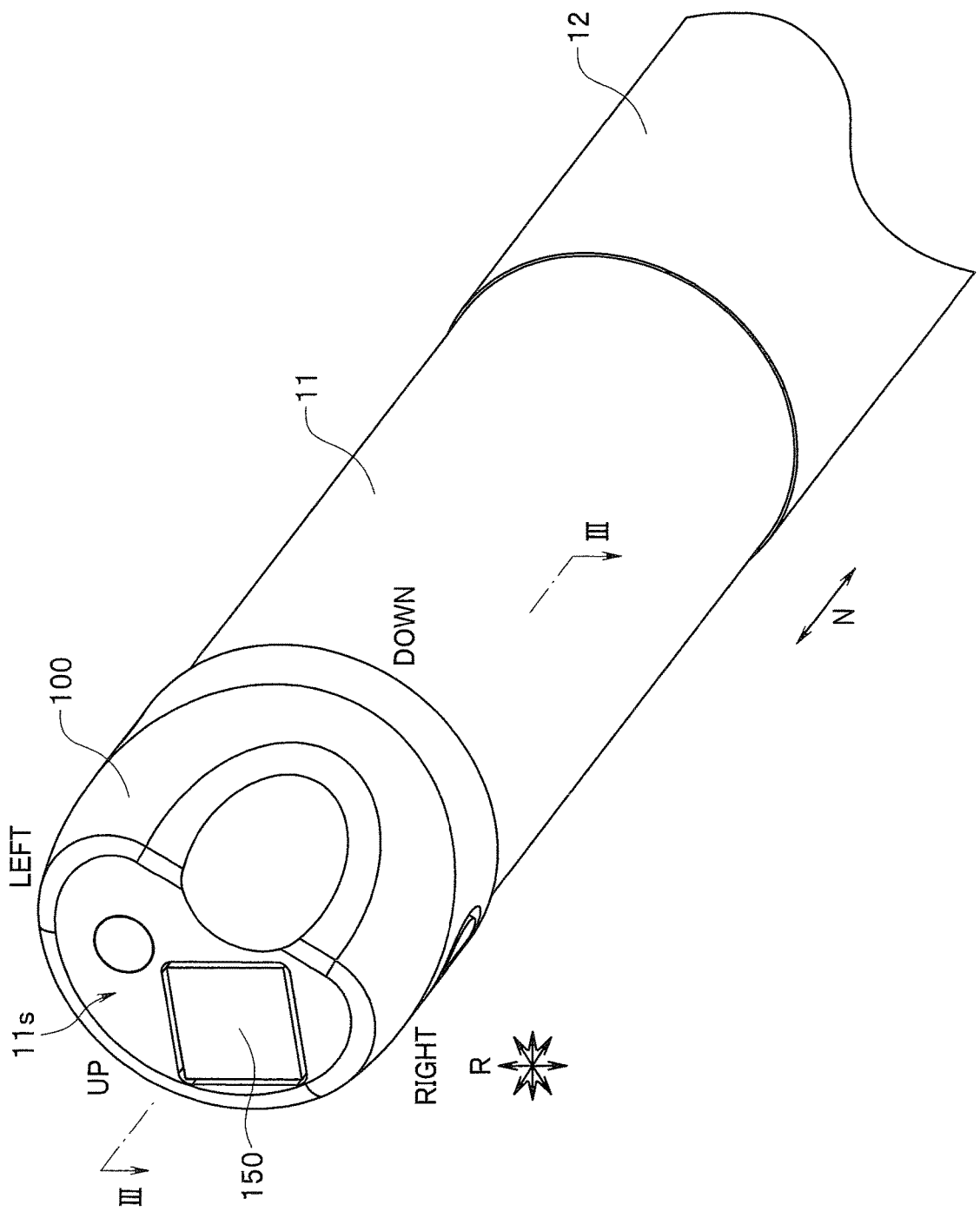
FIG. 2 is an enlarged partial perspective view of a distal end side of the insertion portion of the endoscope illustrated in FIG. 1.
Figure 3:
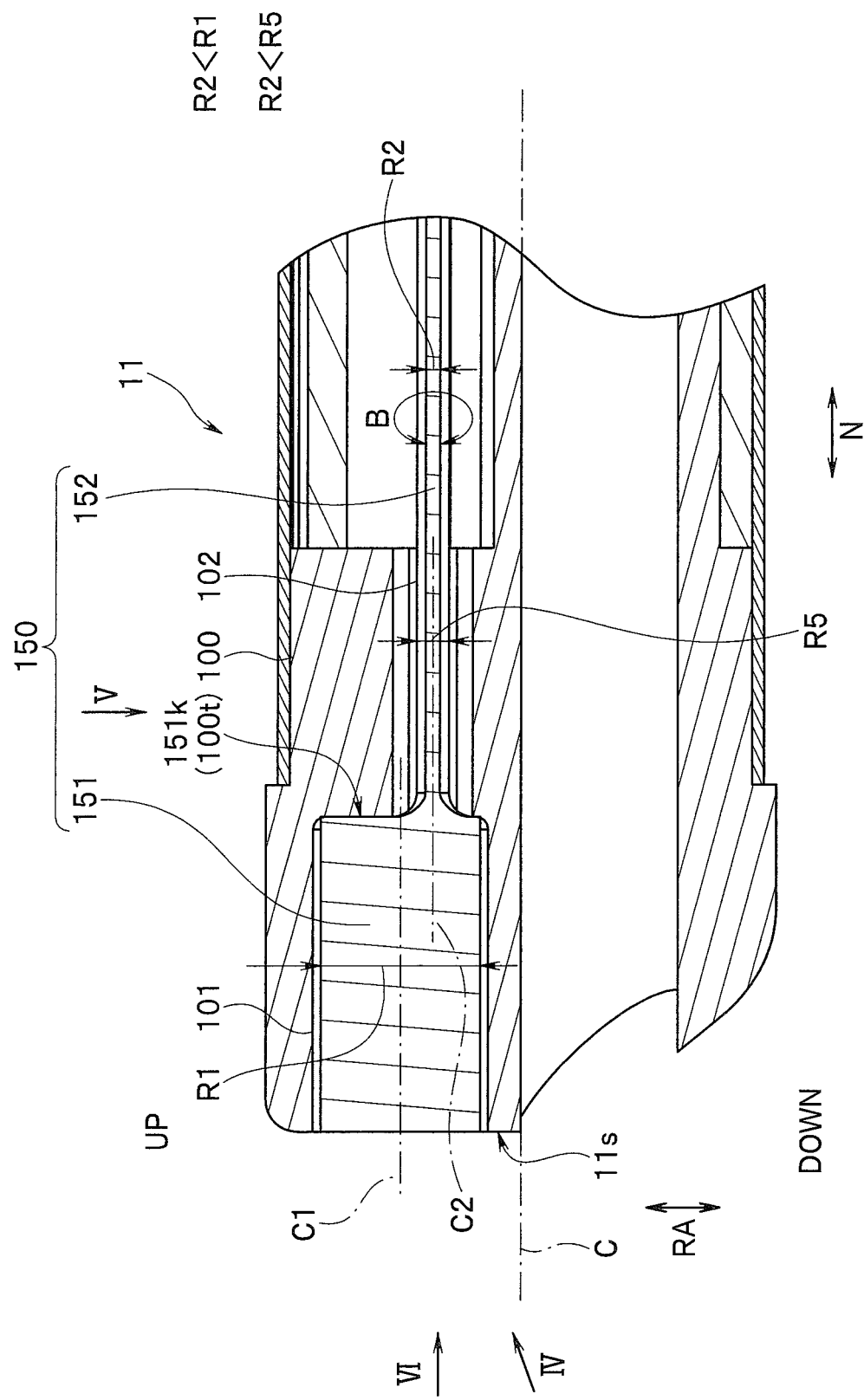
FIG. 3 is a partial sectional view of a distal end portion of the insertion portion taken along a line in FIG. 2.

Next, a configuration of the distal end side of the insertion portion 2 is illustrated with reference to FIGS. 2 to 7. FIG. 2 is an enlarged partial perspective view illustrating the distal end side of the insertion portion of the endoscope in FIG. 1; FIG. 3 is a partial sectional view of the distal end portion of the insertion portion taken along a line in FIG. 2; and FIG. 4 is a partial perspective view of the distal end side of the insertion portion as viewed along an arrow IV in FIG. 3 in a state where the image pickup unit is removed from FIG. 3.

Figure 5:
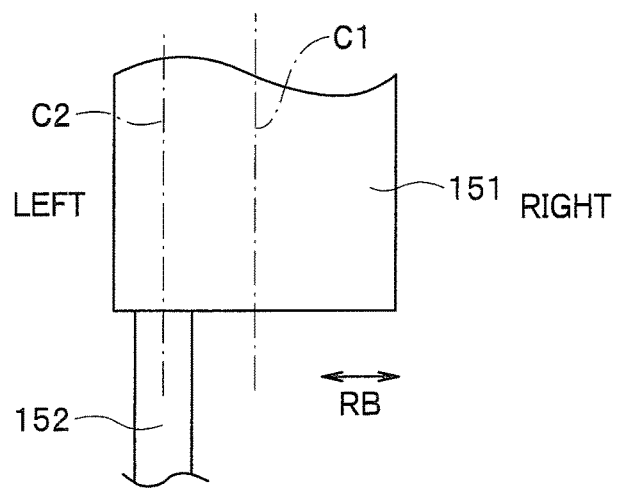
FIG. 5 is a top view schematically illustrating a drawing position of the image pickup cable from the observation unit illustrated in FIG. 3 as viewed along an arrow V in FIG. 3.
Figure 6:
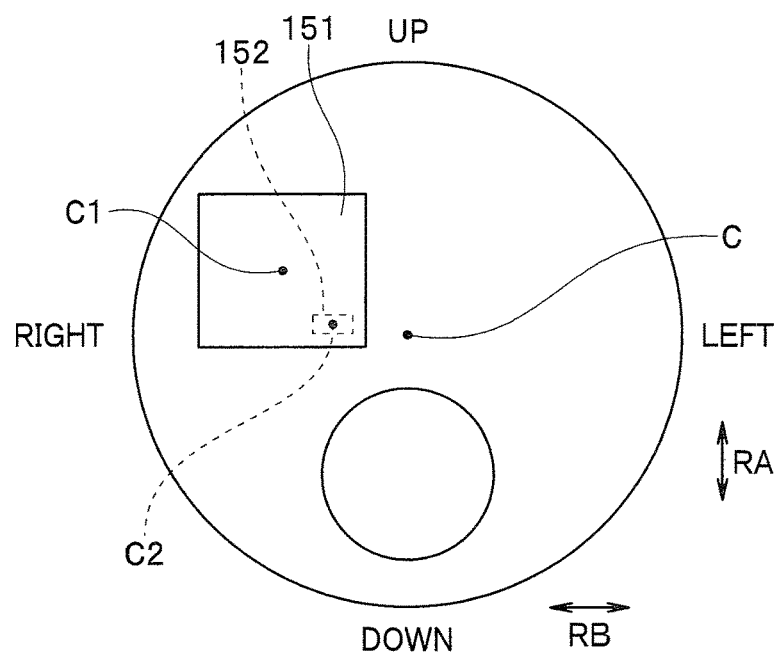
FIG. 6 is a front view schematically illustrating the drawing position of the image pickup cable from the observation unit illustrated in FIG. 3 as viewed along an arrow VI in FIG. 3.

FIG. 5 is a top view schematically illustrating a drawing position of the image pickup cable from the observation unit illustrated in FIG. 3 as viewed along an arrow V in FIG. 3; FIG. 6 is a front view schematically illustrating the drawing position of the image pickup cable from the observation unit illustrated in FIG. 3 as viewed along an arrow VI in FIG. 3; and FIG. 7 is a partial perspective view illustrating a modification in which the image pickup cable illustrated in FIG. 3 is configured in a flat-plate shape.

Figure 4:
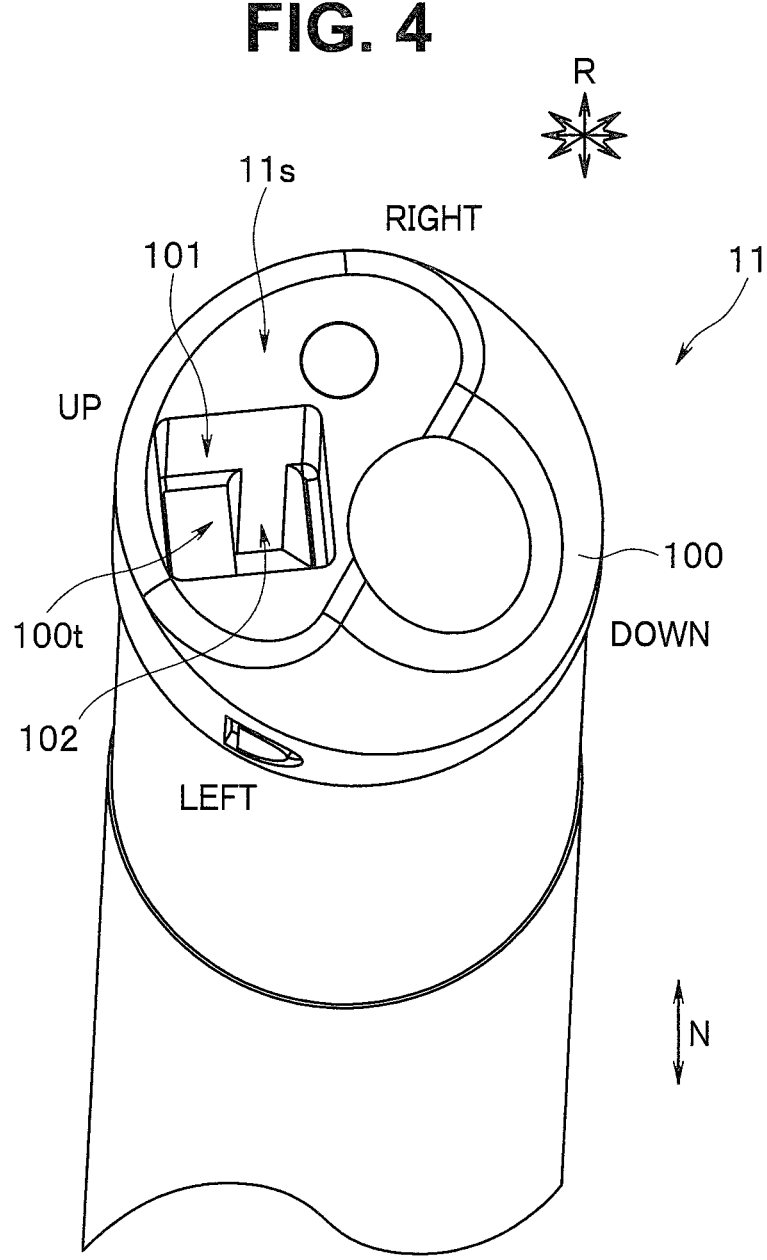
FIG. 4 is a partial perspective view of the distal end side of the insertion portion when viewed along an arrow IV in FIG. 3 in a state in which the image pickup unit is removed from FIG. 3.

As illustrated in FIGS. 2 to 4, the distal end portion 11 is provided with a distal end frame member 100, and an image pickup unit 150 is provided in the distal end frame member 100.

As illustrated in FIG. 3, the image pickup unit 150 includes, as main components, an observation unit 151 which is a non-circular large outer size member having a first central axis C1 and has a first outer size R1, and an image pickup cable 152 which is a small outer size member having a second central axis C2 offset from the first central axis C1 and a second outer size (diameter) R2 smaller than the first outer size R1 (R2<R1), and connected to a proximal end of the observation unit 151.

Figure 7:
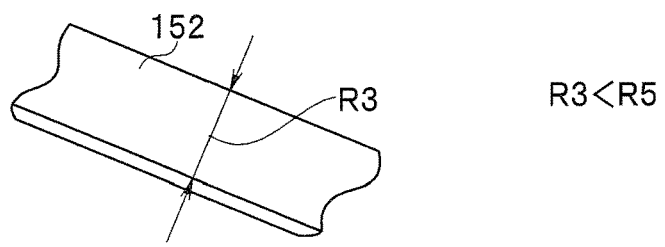
FIG. 7 is a partial perspective view illustrating a modification in which the image pickup cable illustrated in FIG. 3 is configured in a flat-plate shape.

As illustrated in FIG. 7, the image pickup cable 152 is not limited to a circular outer shape. The cable may be configured with a flat-plate outer shape so that a cable width, that is, an outer diameter created by rotating the cable, is R3.

Referring back to FIG. 3, the distal end frame member 100 includes a first hole 101 in which the observation unit 151 is provided, and a second hole 102 connected to a proximal end of the first hole 101, having the image pickup cable 152 provided therein, and having a hole size (diameter) R5.

The observation unit 151 and the image pickup cable 152 are inserted into the first hole 101 and the second hole 102, respectively from a front of the distal end surface 11s of the distal end portion 11, and are fixed to the first hole and the second hole, respectively by adhesive or the like.

The observation unit 151 includes a plurality of optical systems, an image pickup unit, an electric substrate, a frame member for holding these, and the like (all not illustrated). The observation unit 151 is fixed to the first hole 101 in such a manner that a position in a longitudinal axis direction N is determined by a configuration described later so that an objective lens positioned most forward among the plurality of optical systems is exposed outside the distal end surface 11s.

As illustrated in FIGS. 3 and 4, outer size of the first hole 101 is slightly larger than the first outer size R1 of the observation unit 151 provided therein, and an outer shape of the first hole is formed in a shape in accordance with the outer shape of the non-circular observation unit 151 (for example, a rectangular shape in FIGS. 2 and 4).

The image pickup cable 152 is drawn from an electric substrate (not illustrated) in the observation unit 151, that is, a distal end of the image pickup cable 152 is electrically connected and fixed to the electrical substrate, and a proximal end of the image pickup cable 152 extends to the connector described above (not illustrated).

The diameter R5 of the second hole 102 is formed to be larger than a diameter created by rotating the image pickup cable 152 around the second central axis C2, for example, larger than R2 when the outer shape of the image pickup cable 152 is circular, and larger than R3 when the image pickup cable is in a flat-plate shape as illustrated in FIG. 7.

Therefore, the second hole 102 has a shape in which the image pickup cable 152 is rotatable together with the observation unit 151 in a state in which the image pickup cable 152 is provided in the second hole 102.

The second central axis C2 is offset with respect to the first central axis C1 toward a center C in a radial direction R of the distal end frame member 100, when the image pickup cable 152 is provided in the second hole 102 and the observation unit 151 is provided in the first hole 101.

That is, an extraction position of the image pickup cable 152 with respect to the observation unit 151 is offset toward the center C.

Specifically, as illustrated in FIGS. 3 and 6, in an UP-DOWN direction RA in the radial direction R, the second central axis C2 is offset toward the DOWN direction with respect to the first central axis C1. As illustrated in FIGS. 5 and 6, in a RIGHT-LEFT direction RB in the radial direction R, the second central axis C2 is offset toward the LEFT direction with respect to the first central axis C1.

This is because when the second central axis C2 is arranged to be offset toward the UP direction and the RIGHT direction with respect to the first central axis C1, contrary to the above, the image pickup cable 152 is arranged near a periphery of the distal end portion 11 in a case that the image pickup unit 150 in the distal end frame member 100 is arranged at the position illustrated in FIGS. 2 to 4 and 6, so that the diameter of the distal end portion 11 is prevented from being small.

In other words, when the second central axis C2 is offset toward the DOWN direction and the LEFT direction with respect to the first central axis C1, it is possible to reduce the diameter of the distal end portion 11 in a case that the image pickup unit 150 in the distal end frame member 100 is arranged at the position illustrated in FIGS. 2 to 4 and 6.

Depending on the arrangement position of the image pickup unit 150 in the distal end frame member 100, the offset direction of the second central axis C2 is not limited to that illustrated in FIG. 6, and may be offset toward the center C in the radial direction R in order to reduce the diameter of the distal end portion 11.

In a connection portion between the first hole 101 and the second hole 102, a contact surface 100t, with which a proximal end portion 151k of the observation unit 151 is brought into contact when the image pickup cable 152 is provided in the second hole 102, is formed.

The contact surface 100t positions the observation unit 151 provided in the first hole 101 in the longitudinal axis direction N when the proximal end portion 151k is brought into contact with. Specifically, the contact surface 100t positions the above-described objective lens in the observation unit 151 so as to be exposed outside the distal end surface 11s.

Since the other configurations of the endoscope 1 are the same as those in the conventional one, detailed description thereof will be omitted.

When the image pickup unit 150 is assembled into the distal end frame member 100 configured as described above, an operator firstly fits the image pickup cable 152 into the second hole 102 through the first hole 101 as illustrated in FIG. 4.

Thereafter, the operator fits the observation unit 151 into the first hole 101 until the proximal end portion 151k of the observation unit 151 comes into contact with the contact surface 100t.

During this operation, when the operator fits the image pickup cable 152 into the second hole 102 in a wrong fitting direction in a circumferential direction B of the image pickup cable 152, the observation unit 151 cannot be fitted into the first hole 101.

In this case, the operator visually recognizes that the fitting direction of the image pickup cable 152 is wrong, and can rotate the image pickup cable 152 in the second hole 102 since the size (diameter) R5 of the second hole 102 is larger than the outer sizes (diameters) R2 and R3 created by rotating the image pickup cable 152 (R5>R2, R3). Consequently, the image pickup cable 152 is rotated together with the observation unit 151 in a direction in which the observation unit 151 can be fitted into the first hole 101, and then the observation unit 151 is fitted into the first hole 101.

Finally, after confirming that the display direction of the image of the object picked up by the observation unit is correct on a monitor (not illustrated), the operator fixes the observation unit 151 and the image pickup cable 152 to the first hole 101 and the second hole 102, respectively by adhesive, for example.

In the present embodiment, the contact surface 100*t* with which the proximal end portion 151*k* of the observation unit 151 is brought into contact is formed in the distal end frame member 100.

According to this configuration, when the image pickup unit 150 is assembled from the distal end surface 11*s* side into the first hole 101 and the second hole 102 in the distal end frame member 100, the observation unit 151 in the first hole 101, that is the image pickup unit 150 in a longitudinal axis direction N, can be easily positioned by simply bringing the proximal end portion 151*k* of the observation unit 151 fitted into the first hole 101 contact with the contact surface 100*t*.

Further, in the present embodiment, the second central axis C2 of the second hole 102 is offset from the first central axis C1 of the first hole 101.

According to this configuration, in a case that the image pickup unit 150 is assembled from the distal end surface 11*s* side into the first hole 101 and the second hole 102 in the distal end frame member 100, when the image pickup cable 152 is fitted into the second hole 102 in the wrong direction in the circumferential direction B, the observation unit 151 cannot be fitted into the first hole 101. Consequently, the operator can easily visually recognize that the assembling direction is incorrect before fixing the image pickup unit and displaying the image of the object on the monitor.

Furthermore, in the present embodiment, the second hole 102 has a shape in which the image pickup cable 152 is rotatable together with the observation unit 151 in a state in which the image pickup cable 152 is provided in the second hole 102.

According to this configuration, even when the image pickup cable 152 is fitted into the second hole 102 in the wrong direction in the circumferential direction B, the image pickup cable 152 can be rotated together with the observation unit 151. Consequently, since the operator can fit the observation unit 151 into the first hole 101 and rotate it in a direction as the display direction is to be correct, it is not necessary to pull out the image pickup unit 150 from the front and fit it again in the correct direction as in the conventional one.

This configuration is particularly effective when the image pickup cable 152 is configured in a flat-plate shape as illustrated in FIG. 7, because the image pickup cable 152 is easily fitted into the second hole 102 in the wrong opposite direction by 180°.

As described above, it is possible to provide the insertion portion 2 of the endoscope having the configuration capable of easily and accurately assembling the image pickup unit 150 into the distal end frame member 100 without confirming the assembling direction.

The present invention is not limited to the embodiments described above, and various changes and modifications can be made in a range without departing from the gist of the present invention.

What is claimed is:

1. An insertion portion of an endoscope comprising:
   an image pickup unit having;
      a non-circular large outer size member having a first central axis and a first outer size; and
      a small outer size member having a second central axis offset from the first central axis, the small outer size member having a second outer size smaller than the first outer size and connected to a proximal end of the large outer size member; and
   a distal end frame member having a first hole in which the large outer size member is provided, and a second hole provided in a proximal end of the first hole and in which the small outer size member is provided, wherein
   the second hole has a shape in which the small outer size member is rotatable together with the large outer size member in a state where the small outer size member is provided in the second hole.

2. The insertion portion of the endoscope according to claim 1, wherein
   the small outer size member is configured in a flat-plate shape.

3. The insertion portion of the endoscope according to claim 2, wherein
   the second hole is formed to have a size larger than an outer diameter created by rotating the small outer size member around the second central axis.

4. The insertion portion of the endoscope according to claim 1, wherein
   the second central axis is offset toward the center in the radial direction of the distal end frame member with respect to the first central axis, when the small outer size member is provided in the second hole and the large outer size member is provided in the first hole.

5. The insertion portion of the endoscope according to claim 1, wherein
   the large outer size member and the small outer size member are inserted from front, respectively into and fixed to the first hole and the second hole.

6. The insertion portion of the endoscope according to claim 1, wherein
   the distal end frame member includes a contact surface with which a proximal end portion of the large outer size member is brought into contact when the small outer size member is provided in the second hole.

\* \* \* \* \*